United States Patent [19]

Schwamborn et al.

[11] Patent Number: 4,609,648
[45] Date of Patent: Sep. 2, 1986

[54] HALOGENOALKYLCARBAMIC ACID ESTER PESTICIDES

[75] Inventors: Michael Schwamborn, Cologne; Hermann Hagemann, Leverkusen; Gerhard Heywang, Bergisch Gladbach; Wolfgang Behrenz, Overath, all of Fed. Rep. of Germany

[73] Assignee: Bayer Aktiengesellschaft, Leverkusen, Fed. Rep. of Germany

[21] Appl. No.: 630,492

[22] Filed: Jul. 13, 1984

[30] Foreign Application Priority Data

Jul. 26, 1983 [DE] Fed. Rep. of Germany ....... 3326873

[51] Int. Cl.$^4$ .................. C07C 125/065; A01N 47/10
[52] U.S. Cl. ........................................ 514/84; 514/86; 514/100; 514/132; 514/136; 514/465; 514/469; 514/477; 514/479; 560/161; 558/444
[58] Field of Search ................... 560/161; 260/465.4; 424/300, 304; 514/479, 478, 84, 86, 100, 132, 136, 465, 469, 477

[56] References Cited

FOREIGN PATENT DOCUMENTS 633594 6/1962 Belgium .
1203534 6/1962 Fed. Rep. of Germany ...... 560/161

OTHER PUBLICATIONS

Frear, J. of Econ. Ent., 40, pp. 736–741 (1947).

*Primary Examiner*—Michael L. Shippen
*Attorney, Agent, or Firm*—Sprung Horn Kramer & Woods

[57] ABSTRACT

Halogenoalkylcarbamic acid esters of the formula

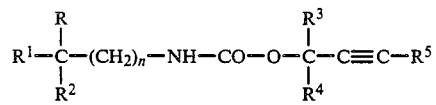

in which

R, $R^1$ and $R^2$ independently of one another represent methyl which is optionally substituted by halogen, at least one of the methyl groups R, $R^1$ and $R^2$ being substituted by at least one halogen atom, $R^3$, $R^4$ and $R^5$ are identical or different and individually represent hydrogen or optionally substituted alkyl and n represents 0 or 1, synergize the action of known arthropodicides.

12 Claims, No Drawings

HALOGENOALKYLCARBAMIC ACID ESTER PESTICIDES

The present invention relates to halogenoalkylcarbamic acid esters, processes for their preparation and their use as agents for combating pests, preferably for combating arthropods, in particular insects, mites and arachnids.

Synergistic mixtures of insecticidal active compounds, for example of pyrethroids, with certain methylenedioxyphenyl derivatives, for example piperonyl butoxide, as synergistic agents have already been disclosed (compare, for example, K. Naumann, Chemie der Pflanzenschutz-und Schädlingsbekämpfungsmittel (Chemistry of the Plant Protection Agents and Agents for combating pests), Springer Verlag Berlin, Volume 7 (1981) pages 3–6). Certain N-arylcarbamic acid alkinyl esters (compare DE-A (German Published Specification) No. 2,041,986) and certain N-alkylcarbamic acid alkinyl esters (compare BE-A (Belgian Published Specification) No. 633,594) have also been described as synergistic agents. However, the activity of these compounds under the conditions which arise in practice is not always completely satisfactory.

The new carbamic acid esters of the general formula (I)

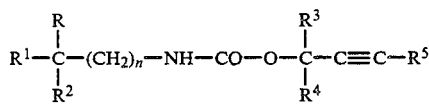

in which
  R, $R^1$ and $R^2$ independently of one another represents methyl which is optionally substituted by halogen, at least one of the methyl groups R, $R^1$ and $R^2$ being substituted by at least one halogen atom,
  $R^3$, $R^4$ and $R^5$ are identical or different and individually represent hydrogen or optionally substituted alkyl and
  n represents 0 or 1,
have now been found.

The new compounds of the formula (I) can be used as synergistic agents in agents for combating pests which additionally contain arthropodicides having a preferential action against insects and arachnids, in particular against insects.

Virtually all the customary active compounds are suitable as the arthropodicides (substances having an action against arthropods) (compare, for example, K. H. Büchel, Pflanzenschutz und Schäadlingsbekämpfungsmittel (Plant Protection and Agents for combating pests), Thieme Verlag Stuttgart, 1977, and Farm Chemicals Handbook 1979, Meister Publishing Co., Willougby, 1979).

It has furthermore been found that the new carbamic acid esters of the general formula (I)

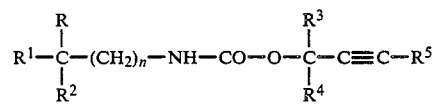

in which
  R, $R^1$ and $R^2$ independently of one another represents methyl which is optionally substituted by halogen, at least one of the methyl groups R, $R^1$ and $R^2$ being substituted by at least one halogen atom,
  $R^3$, $R^4$ and $R^5$ are identical or different and individually represent hydrogen or optionally substituted alkyl and
  n represents 0 or 1,
are obtained when alkyl isocyanates of the general formula (II)

in which
  R, $R^1$, $R^2$ and n have the abovementioned meaning, are reacted with alkinyl alcohols of the general formula (III)

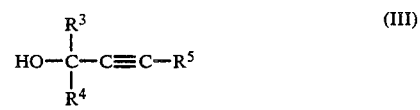

in which
  $R^3$, $R^4$ and $R^5$ have the abovementioned meaning, if appropriate in the presence of an aprotic diluent and if appropriate in the presence of a catalyst, at temperatures between 0° and 120° C.

The methyl groups R, $R^1$ and $R^2$ optionally substituted by halogen are identical or different and contain 1 to 3, preferably 1 or 2 and particularly preferably 1, halogen atom per methyl group, it being possible for the halogen atoms to be identical or different. Possible halogen atoms are fluorine, chlorine, bromine and or iodine, preferably fluorine and/or chlorine.

R, $R^1$ and $R^2$ preferably represent $CH_3$, $CH_2Cl$ and/or $CH_2F$, at least one of the groups R, $R^1$ and $R^2$ denoting $CH_2Cl$ or $CH_2F$. The halogen atoms in the methyl groups R, $R^1$ and $R^2$ are particularly preferably identical.

Especially preferred parts of the molecule $RR^1R^2C$— which may be mentioned are: $(CH_3)_2CH_2FC$—, $CH_3(CH_2F)_2C$—, $(CH_2F)_3C$—, $(CH_3)_2CH_2ClC$—, $CH_3(CH_2Cl)_2C$— and $(CH_2Cl)_3C$—.

If n represents 0, the $RR^1R^2C$ group in the molecule of the formula (I) is bonded directly to the NH group. If n represents 1, the $RR^1R^2C$ group is bonded to the NH group via a $CH_2$ group.

Optionally substituted alkyl $R^3$, $R^4$ and $R^5$ is straight-chain or branched optionally substituted alkyl with preferably 1–8, in particular 1–5 and particularly preferably 1–3, carbon atoms. Examples which may be mentioned are optionally substituted methyl, ethyl, n- and i-propyl and n-, iso- and tert.-butyl, these radicals preferably being unsubstituted.

The alkyl radicals mentioned in the definition of $R^3$ ahd $R^4$ can carry one or more, preferably 1 to 3 and in particular 1 or 2, identical or different substituents. Examples of substituents which may be mentioned are: alkoxy with preferably 1 to 4, in particular 1 or 2, carbon atoms, such as methoxy, ethoxy, n- and iso-propoxy and n-, iso- and tert.-butoxy; alkylthio with preferably 1 to 4, in particular 1 or 2, carbon atoms, such as methylthio, ethylthio, n- and iso-propylthio and n-, iso- and tert.-butylthio; halogenoalkyl with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethyl; halogen, preferably fluorine, chlorine, bromine and iodine, in particular chlorine and bromine; cyano; nitro; and alkoxycarbonyl with preferably 2 to 4, in particular 2 or 3, carbon atoms, such as methoxycarbonyl and ethoxycarbonyl.

The alkyl radical mentioned in the definition of $R^5$ can carry one or more, preferably 1 to 3 and in particular 1 or 2, identical or different substituents. Examples of substituents which may be mentioned are: alkoxy with preferably 1 to 4, in particular 1 or 2, carbon atoms, such as methoxy, ethoxy, n- and iso-propoxy and n-, iso- and tert.-butoxy; alkylthio with preferably 1 to 4, in particular 1 or 2, carbon atoms, such as methylthio, ethylthio, n- and iso-propylthio and n-, iso- and tert.-butylthio; halogenoalkyl with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethyl; halogen, preferably fluorine, chlorine, bromine and iodine, in particular chlorine and bromine; cyano; nitro; and alkoxycarbonyl with preferably 2 to 4, in particular 2 or 3, carbon atoms, such as methoxycarbonyl and ethoxycarbonyl.

The radicals $R^3$, $R^4$ and $R^5$ are preferably unsubstituted. $R^3$, $R^4$ and $R^5$ particularly preferably represent hydrogen.

The methyl groups R, $R^1$ and $R^2$ which are substituted by halogen preferably contain one halogen atom as the substituent.

Preferred carbamic acid esters of the general formula (I) are those in which

R, $R^1$ and $R^2$ independently of one another represent methyl which is optionally substituted by fluorine or chlorine, at least one of the methyl groups R, $R^1$ and $R^2$ being substituted by at least one fluorine or chlorine atom, $R^3$, $R^4$ and $R^5$ are identical or different and individually represent hydrogen or an alkyl radical which has 1 or 2 carbon atoms and is optionally substituted by halogen, cyano, $C_1$–$C_4$-alkoxy, $C_1$–$C_4$-alkylthio or trifluoromethyl and n represents 0 or 1.

The invention particularly preferably relates to carbamic acid esters of the general formula (I) in which R, $R^1$ and $R^2$ independently of one another represent $CH_3$, $CH_2Cl$ and/or $CH_2F$, at least one of the radicals R, $R^1$ and $R^2$ representing $CH_2Cl$ or $CH_2F$, $R^3$, $R^4$ and $R^5$ represent hydrogen and n represents 0 or 1.

If, for example, bis-2,2-fluoromethyl-3-fluoropropyl isocyanate and propargyl alcohol are used as starting substances, the process according to the invention can be illustrated by the following equation:

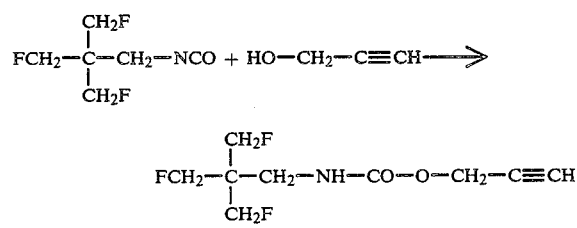

The starting materials can preferably be used in equimolar amounts in the process according to the invention. However, it is also possible simultaneously to use one of the components as the diluent.

Virtually all the aprotic solvents are suitable diluents in the process according to the invention. Preferred solvents which may be mentioned here are ketones, such as acetone, optionally halogenated aliphatic or aromatic hydrocarbons, such as methylene chloride or toluene, nitriles, such as acetonitrile, and mixtures thereof. However, the process can also be carried out without using a solvent.

Triethylamine, diazabicyclooctane (DABCO) or dibutyl-tin laurate are optionally added to the reaction mixture as catalysts.

The reaction temperature is kept between about 0° and 120° C., preferably between about 0° and 60° C., in the process according to the invention. The process is preferably carried out under normal pressure.

The starting compounds of the formula (II) are known and/or can be prepared in the customary manner by processes and methods which are known per se (compare, for example, Methoden der organischen Chemie (Methods of Organic Chemistry) (Houben-Weyl-Müller) 4th edition, Volume 8 (1952) page 119 et seq., DE-A (German Published Specification) No. 2,045,906 and DE-A (German Published Specification) No. 2,045,907).

The new isocyanates of the formula (II) in which R, $R^1$ and/or $R^2$ represent fluorinated methyl groups and n represents 0 are obtained from the corresponding chloropivaloyl chlorides. For this, the known pivaloyl chlorides ($RR^1R^2C$—$COCl$), in which R, $R^1$ and/or $R^2$ denote chlorinated methyl groups, are reacted with alkali metal fluorides, such as potassium fluoride, at elevated temperature, for example at 200° C., in an organic solvent, such as tetramethylene sulphone, the particular corresponding equimolar amount of alkali metal fluoride, or a slight excess, being used, based on the number of chlorine atoms to be replaced by fluorine (chlorine atoms of the methyl groups and chlorine atom of the acid chloride part). The fluoropivaloyl fluorides obtained in this manner are converted into the isocyanates in a known manner (compare, for example, Methoden der Organischen Chemie (Methods of Organic Chemistry), Houben-Weyl, Volume IX/1 (1957), pages 867–872, Thieme-Verlag, Stuttgart). For this, the fluoropivaloyl fluorides are reacted, for example, in a solution in acetone with approximately molar amounts of sodium azide (in aqueous solution) at about 0° to 20° C. The mixture is then extracted with toluene, the toluene phase is separated off and dried with sodium sulphate and the toluene solution is heated to the boiling point. The isocyanate formed, of the formula (II), can be reacted directly in the toluene solution or isolated by distillation.

The new isocyanates of the formula (II) in which R, $R^1$ and/or $R^2$ represent fluorinated methyl groups and n represents 1 can likewise be obtained from the above-mentioned fluoropivaloyl fluorides (or corresponding fluoropivaloyl chlorides).

For this, the fluoropivaloyl acid halides ($RR^1R^2C$ CO Hal, Hal is preferably F) are treated with aqueous ammonia solution at about 0° to 10° C. in methylene chloride, the fluoropivalic acid amides ($RR^1R^2C$—$CONH_2$) precipitating. The pivalic acid amides are filtered off with suction, dried and then reacted with phosphorus pentoxide at temperatures of about 160° to 200° C. under reduced pressure (about 70 mbar), whereupon the fluoropivalic acid nitriles (RR$^1$R$^2$C—C≡N) are formed, and are isolated by distillation. These nitriles are then hydrogenated with hydrogen in the presence of a catalyst (such as Raney nickel) under about 80 to 90 bar at temperatures of about 35° to 50° C. in methanol to give the neopentylamines (RR$^1$R$^2$—CH$_2$—NH$_2$), which are obtained by filtering off the catalyst and subsequently distilling off the solvent. These neopentylamines (if appropriate in the form of the hydrochlorides) are converted to neopentyl isocyanates by reacting the neopentylamines with phosgene (COCl$_2$), for example in chlorobenzene at temperatures between 20° C. and the boiling point of the reaction mixture. The neopentyl isocyanates (RR$^1$R$^2$C—CH$_2$—NCO) are isolated by distillation and if appropriate purified. The conversions of the fluoropivaloyl acid halides (RR$^1$R$^2$CCOHal) into the neopentyl isocyanates (RR$^1$R$^2$C—CH$_2$—NCO) can also be carried out using other generally customary methods of organic chemistry which deviate from the above in the individual stages.

Starting compounds of the formula (III) are known and can be prepared in the customary manner by processes which are known per se (compare W. Reppe J. Liebigs Ann. Chem. 569, 1 (1955), W. Ried, Angew. Chem. 76, 973 (1964) and W. Ried et al. Chem. Ber. 98, 245 (1965)).

When mixed with substances of any desired structure which are active against arthropods, the carbamic acid esters of the general formula (I) display powerful synergistic actions which enable them to be used in agents for combating pests.

The carbamic acid esters of the general formula (I) are preferably used together with arthropodicidal
 1. carbamic acid esters and/or
 2. carboxylic acid esters, including the natural and synthetic pyrethroids, and/or
 3. phosphorus compounds, such as phosphoric acid esters and phosphonic acid esters, including the thio and dithio compounds, and/or
 4. halogeno-(cyclo)-alkanes, such as, for example, hexachlorocyclohexane.

Surprisingly, the action of the new active compound combinations according to the invention against arthropods is substantially higher than the action of the individual components or the sum of the actions of the individual components. It is furthermore substantially higher than the action of active compound combinations with the known commercially available synergistic agent piperonyl butoxide. The carbamic acid esters which can be used according to the invention also exhibit excellent synergistic activity not only with one class of active compound but with active compounds from the most diverse groups of chemical substances.

The synergistic action of the compounds of the general formula (I) is particularly preferentially exhibited with
 (1) carbamic acid esters of the formula (IV)

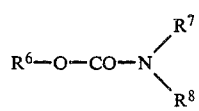

(IV)

in which
 R$^6$ represents an optionally substituted carbocyclic or heterocyclic aromatic radical or an optionally substituted oxime radical (the radicals R$^6$ described below being preferred),
 R$^7$ represents C$_1$–C$_4$-alkyl and
 R$^8$ represents hydrogen, C$_1$–C$_4$-alkyl or a radical Y,
wherein
 Y represents the radical —CO—R$^9$,
wherein
 R$^9$ represents halogen, C$_1$–C$_4$-alkyl, C$_1$–C$_4$-alkoxy, C$_3$–C$_5$-alkenoxy, C$_3$–C$_5$-alkinoxy, C$_1$–C$_4$-alkylthio, C$_1$–C$_4$-alkylamino, di-C$_1$–C$_4$-alkylamino or C$_1$–C$_4$-alkyl-hydroxylamino, or phenoxy, phenylthio or phenylamino which is optionally substituted by halogen, nitro, cyano, trifluoromethyl, C$_1$–C$_4$-alkyl, C$_1$–C$_4$-alkoxy, C$_1$–C$_4$-alkylenedioxy, C$_1$–C$_4$-alkylthio or C$_1$–C$_4$-alkoxy-carbonyl, or 2,3-dihydro-2,2-dimethyl-7-benzofuranyl or the radical

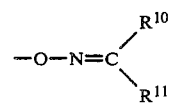

wherein
 R$^{10}$ represents hydrogen, C$_1$–C$_4$-alkyl or di-C$_1$–C$_4$-alkylamino-carbonyl and
 R$^{11}$ represents C$_1$–C$_4$-alkyl, C$_1$–C$_4$-alkylthio, cyano-C$_1$–C$_4$-alkylthio or C$_1$–C$_4$-alkylthio-C$_1$–C$_4$-alkyl, or
 the two radicals R$^{10}$ and R$^{11}$ together represent C$_2$–C$_8$-alkanediyl which is optionally interrupted by oxygen, sulphur, SO or SO$_2$, or
in which
 Y represents the radical —S$_n$(O)$_m$—R$^{12}$,
wherein
 n represents 1 or 2,
 m represents 0, 1 or 2 and
 R$^{12}$ represents optionally halogen-substituted C$_1$–C$_4$-alkyl, C$_3$–C$_5$-alkenyl, C$_3$–C$_5$-alkinyl or C$_3$–C$_6$-cycloalkyl, or phenyl, benzyl or phenethyl which is optionally substituted by halogen, cyano, nitro, trifluoromethyl, trifluoromethoxy, trifluoromethylthio, C$_1$–C$_4$-alkyl or C$_1$–C$_4$-alkoxy, or the radical

wherein
 R$^{13}$ represents C$_1$–C$_4$-alkyl, C$_3$–C$_5$-alkenyl, C$_3$–C$_5$-alkinyl, C$_3$–C$_6$-cycloalkyl or benzyl and R$^{14}$ represents C$_1$–C$_4$-alkyl, C$_3$–C$_5$-alkenyl, C$_3$–C$_5$-alkinyl, C$_3$–C$_6$-cycloalkyl, benzyl, phenethyl, halogenocarbonyl, formyl, C$_1$–C$_4$-alkyl-carbonyl, C$_1$–C$_4$-alkoxy-carbonyl, C$_1$–C$_4$-alkoxyphenoxy-carbonyl, C$_3$–C$_5$-alkinoxy-carbonyl, C$_3$–C$_5$-alkenoxycarbonyl, C$_1$–C$_4$-alkylthiocarbonyl, C$_1$–C$_4$-alkylaminocarbonyl, C$_1$–C$_4$-alkyl-hydroxylamino-carbonyl, C$_1$–C$_{10}$-alkyl-phenoxycarbonyl, di-C$_1$–C$_4$-alkylamino-carbonyl, phenylthiocarbonyl, phenoxycarbonyl, or 2,3-dihydro-2,2-dimethyl-7-benzofuranyloxy-carbonyl, or phenylsulphenyl, phenylsulphinyl, phenylsulphonyl or phenyl which is optionally substituted by halogen, cyano, nitro, trifluoromethyl, C$_1$–C$_{10}$-alkyl or C$_1$–C$_4$-alkoxy, or the radical $$-CO-O-N=C\begin{matrix}R^{15}\\R^{16}\end{matrix}$$

wherein
R[15] has the meaning given above for R[10] and
R[16] has the meaning given above for R[11],
and wherein, furthermore, in the radical $$-N\begin{matrix}R^{13}\\R^{14}\end{matrix}$$

the radicals R[13] and R[14] together represent a hydrocarbon chain which has 3 to 8 carbon atoms and is optionally interrupted by oxygen or sulphur,
and wherein, furthermore,
R[12] can also represent the same radical to which the radical $-S_n(O)_m-R^{12}$ is bonded.

Very particularly preferred active compound components are carbamic acid esters of the formula (IV) in which
R[6] represents a radical from the series comprising phenyl, naphthyl, 2,3-dihydro-7-benzofuranyl, pyrazolyl and pryimidinyl, which is optionally substituted by $C_1$–$C_4$-alkyl, $C_2$–$C_4$-alkenyl, $C_1$–$C_4$-alkoxy, $C_1$–$C_4$-alkoxy-methyl, $C_1$–$C_4$-alkylthio, $C_1$–$C_4$-alkylthio-methyl, $C_1$–$C_4$-alkylamino, di-($C_1$–$C_4$-alkyl)-amino, di-($C_3$–$C_4$-alkenyl)-amino, halogen, dioxolanyl, methylenedioxy and/or by the radical $-N=CH-N(CH_3)_2$,
or in which
R[6] represents an alkylideneamino radical of the formula (Iva)

$$-N=C\begin{matrix}R^{17}\\R^{18}\end{matrix}\quad\text{(IVa)}$$

in which
R[17] and R[18] have the meaning given above for R[10] and, respectively, R[11],
R[7] represents $C_{1-4}$-alkyl and
R[8] represents hydrogen or $C_1$–$C_4$-alkyl (preferably hydrogen).

Examples which may be mentioned of the carbamic acid esters of the formula (IV) are: N-methyl-carbamic acid 2-methyl-phenyl, 2-ethyl-phenyl, 2-iso-propylphenyl, 2-sec-butyl-phenyl, 2-methoxy-phenyl, 2-ethoxyphenyl, 2-isopropoxy-phenyl, 4-methyl-phenyl, 4-ethylphenyl, 4-n-propyl-phenyl, 4-methoxy-phenyl, 4-ethoxyphenyl, 4-n-propoxy-phenyl, 3,4,5-trimethyl-phenyl, 3,5-dimethyl-4-methylthio-phenyl, 3-methyl-4-dimethylaminophenyl, 2-ethylthiomethyl-phenyl, 1-naphthyl, 2,3-dihydro-2,2-dimethyl-7-benzofuranyl, 2,3-(dimethyl-methylenedioxy)-phenyl, 2-(4,5-dimethyl-1,3-dioxolan-2-yl)-phenyl, 1-methylthio-ethylideneamino, 2-methylthio-2-methylpropylideneamino, 1-(2-cyano-ethylthio)-ethylideneamino and 1-methylthiomethyl-2,2-dimethylpropylideneamino ester.

The synergistic action of the compounds of the general formula (I) is also preferentially exhibited with
(2) carboxylic acid esters of the formula (V)

$$R^{19}-CO-O-CH-R^{21}\quad\text{(V)}\\\phantom{R^{19}-CO-O-}|\\\phantom{R^{19}-CO-O-C}R^{20}$$

in which
R[19] represents an open-chain or cyclic alkyl radical which is optionally substituted by halogen, alkyl or cycloalkyl, by alkenyl which is optionally substituted by halogen, alkyl and/or alkoxy, by phenyl or styryl, which are optionally substituted by halogen or optionally halogen-substituted radicals from the series comprising alkyl, alkoxy, alkylenedioxy and/or alkylthio, or by spirocyclically linked, optionally halogen-substituted cycloalk(en)yl, which is optionally benzo-fused,
and in which, furthermore,
R[20] represents hydrogen, alkyl, halogenoalkyl, alkenyl, alkinyl or cyano and
R[21] represents an optionally substituted alkyl or aryl radical or a heterocyclic radical, or, together with R[20] and the carbon atom to which the two radicals are bonded, forms a cyclopentenone ring.

Very particularly preferred active components are carboxylic acid esters of the formula (V) in which
R[19] represents the radical $$\begin{matrix}&&R^{22}\\&&/\\&-CH=C\\&&\backslash\\&&R^{23}\end{matrix}\\H_3C\quad CH_3$$

wherein
R[22] represents hydrogen, methyl, fluorine, chlorine or bromine and
R[23] represents methyl, fluorine, chlorine, bromine, $C_1$–$C_2$-fluoroalkyl or $C_1$–$C_2$-chlorofluoroalkyl, or phenyl which is optionally substituted by halogen and/or optionally halogen-substituted radicals from the series comprising $C_1$–$C_4$-alkyl, $C_1$–$C_4$-alkoxy, $C_1$–$C_4$-alkylthio and/or $C_1$–$C_2$-alkylenedioxy,
or wherein
the two radicals R[22] and R[23] represent $C_2$–$C_5$-alkanediyl (alkylene);
or in which
R[19] represents the radical $$-CH-R^{24},\\|\\R^{25}$$

wherein
R[24] represents phenyl which is optionally substituted by halogen and/or by optionally halogen-substituted radicals from the series comprising $C_1$–$C_4$-alkyl, $C_1$–$C_4$-alkoxy, $C_1$–$C_4$-alkylthio and $C_1$–$C_2$-alkylenedioxy and
R[25] represents isopropyl or cyclopropyl;
or in which
R[19] represents one of the radicals

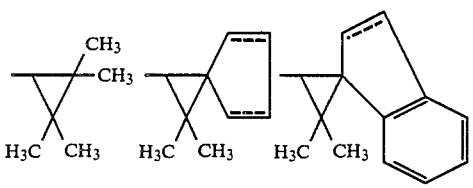

wherein
the dotted lines are intended to indicate possible double bonds, or
$R^{19}$ represents methyl,
and in which, furthermore,
$R^{20}$ represents hydrogen, $C_1$-$C_4$-alkyl, $C_1$-$C_4$-halogenoalkyl, cyano or ethinyl and
$R^{21}$ represents a radical from the series comprising phenyl, furyl and tetrahydrophthalimido, it being possible for these radicals to be substituted by halogen and/or radicals from the series comprising $C_1$-$C_4$-alkyl, $C_2$-$C_4$-alkenyl, $C_1$-$C_4$-alkoxy, $C_2$-$C_4$-alkenoxy, $C_1$-$C_4$-alkylthio, $C_1$-$C_2$-alkylenedioxy, phenoxy and/or benzyl, which can in turn be substituted by halogen,
and wherein
$R^{21}$ preferably represents pentafluorophenyl, 3,4-dichlorophenyl, phenoxyphenyl, which can be substituted in one or both phenyl rings by halogen, or represents tetrahydrophthalimido.

The naturally occurring pyrethroids (such as pyrethreum) are also particularly preferred as carboxylic acid esters of the formula (V).

Examples which may be mentioned of the carboxylic acid esters of the formula (V) are: 2,2,2-trichloro-1-(3,4-dichloro-phenyl)-ethyl acetate, 3,4,5,6-tetrahydrophthalimido-methyl 2,2-dimethyl-3-(2-methyl-propen-1-yl)cyclopropane-carboxylate, 3-phenoxy-benzyl 2,2-dimethyl-3-(2,2-dichlorovinyl)-cyclopropane-carboxylate, α-cyano-3-phenoxy-benzyl 2,2-dimethyl-3-(2,2-dichlorovinyl)cyclopropane-carboxylate, α-cyano-4-fluoro-3-phenoxybenzyl 2,2-dimethyl-3-(2,2-dichlorovinyl)-cyclopropanecarboxylate, pentafluorobenzyl 2,2-dimethyl-3-(2,2-dichlorovinyl)-cyclopropane-carboxylate, α-cyano-3-phenoxybenzyl 2,2-dimethyl-3-(2,2-dibromovinyl)-cyclopropanecarboxylate and α-cyano-3-phenoxy-benzyl 3-methyl-2-(4-chloro-phenyl)-butanoate.

The synergistic action of the compounds of the general formula (I) is furthermore preferentially exhibited with (3) phosphoric acid esters and phosphonic acid esters of the general formula (VI)

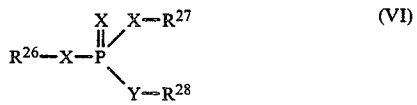

in which
X in each case represents O or S,
Y represents O, S, —NH— or a direct bond between the central P atom and $R^{28}$,
$R^{26}$ and $R^{27}$ are identical or different and represent optionally substituted alkyl or aryl and
$R^{28}$ represents hydrogen, optionally substituted alkyl, aryl, heteroaryl, aralkyl, alkenyl, dioxanyl or an oxime radical or the same radical to which it is bonded.

Particularly preferred phosphoric acid esters and phosphonic acid esters of the formula (VI) are those in which
$R^{26}$ and $R^{27}$ are identical or different and represent $C_1$-$C_4$-alkyl or phenyl,
$R^{28}$ represents hydrogen, alkyl which has 1 to 4 carbon atoms and is optionally substituted by halogen, hydroxyl, cyano, optionally halogen-substituted phenyl, carbamoyl, alkylsulphonyl, alkylsulphinyl, alkylcarbonyl, alkoxy, alkylmercapto, alkoxycarbonyl or alkylaminocarbonyl, the latter with in each case up to 6 carbon atoms, or for alkenyl which has up to 4 carbon atoms and is optionally substituted by halogen, optionally halogen-substituted phenyl or $C_1$-$C_4$-alkoxycarbonyl, or for the radical of the general formula (VIa)

wherein
$R^{29}$ and $R^{30}$ have the meaning given above for $R^{10}$ and, respectively, $R^{11}$, or represent cyano or phenyl,
and in which
$R^{28}$ furthermore represents dioxanyl, which is substituted by the same radical to which $R^{27}$ is bonded, or
$R^{28}$ represents the same radical to which it is bonded, or $R^{28}$ represents phenyl, which is optionally substituted by methyl, nitro, cyano, halogen and/or methylthio, or
$R^{28}$ also particularly preferably represents a heteroaromatic radical, such as pyridinyl, quinolinyl, quinoxalinyl, pyrimidinyl or benzo-1,2,4-triazinyl, which is optionally substituted by $C_1$-$C_4$-alkoxy, $C_1$-$C_4$-alkylthiomethyl, $C_1$-$C_4$-alkyl and/or halogen.

Specific examples which may be mentioned are: O,O-dimethyl or O,O-diethyl O-(2,2-dichloro- or 2,2-dibromo-vinyl) phosphate, O,O-diethyl O-(4-nitro-phenyl) thionophosphate, O,O-dimethyl O-(3-methyl-4-methylthiophenyl) thionophosphate, O,O-dimethyl O-(3-methyl-4-nitro-phenyl) thionophosphate, O-ethyl S-n-propyl O-(2,4-dichlorophenyl) thionophosphate, O-ethyl S-n-propyl O-(4-methylthio-phenyl) thionophosphate, O,O-dimethyl S-(4-oxo-1,2,3-benzo triazin (3)yl-methyl) thionothiolphosphate, O-methyl O-(2-isopropyl-6-methoxy-pyrimidin-4-yl) thionomethanephosphonate, O,O-diethyl O-(2-iso-propyl-6-methylpyrimidin-4-yl) thionophosphate, O,O-diethyl O-(3-chloro-4-methyl-coumarin-7-yl) thionophosphate, O,O-dimethyl 2,2,2-trichloro-1-hydroxy-ethane-phosphonate and O,O-dimethyl S-(methylaminocarbonyl-methyl) thionophosphate.

The synergistic action of the compounds of the general formula (I) is furthermore preferentially exhibited with (4) halogeno(cyclo)-alkanes, such as, for example, hexachlorocyclohexane, 1,1,1-trichloro-2,2-bis-(4-chlorophenyl)-ethane, 1,1,1-trichloro-2,2-bis-(4-methoxyphenyl)-ethane and 1,1-dichloro-2,2-bis-(4-ethylphenyl)-ethane.

The weight ratios of the synergistic agents and active compounds can be varied within a relatively wide range. In general, the compounds of the formula (I) used as synergistic agents are used with the other active compounds in mixing ratios of between 1:100 and 100:1, preferably between 1:5 and 5:1 (parts by weight)

The active compound combinations according to the invention not only have a rapid knock-down action, but also destroy animal pests, especially insects and mites, which are encountered in agriculture, in forestry, in the protection of stored products and of materials, and in the hygiene field. They are active against normally sensitive and resistant species and against all or some stages of development.

The animal pests which can be combated using compounds of the formula (I) include, for example:

From the order of the Isopoda, for example, *Oniscus asellus* and *Porcellio scaber*. From the order of the Thysanura, for example, *Lepisma saccharina*. From the order of the Orthoptera, for example, *Blatta orientalis, Periplaneta americana, Leucophaea maderae, Blattella germanica, Acheta domesticus,* Gryllotalpa spp., *Locusta migratoria migratorioides* and *Schistocerca gregaria*. From the order of the Dermaptera, for example, *Forficula auricularia*. From the order of the Isoptera, for example, Reticulitermes spp. From the order of the Anoplura, for example, *Pediculus humanus corporis,* Haematopinus spp and Llnognathus spp. From the order of the Mallophaga, for example, Trichodectes spp and Damalinea spp. From the order of the Heteroptera, for example, *Cimex lectularius, Rhodnius prolixus* and Triatoma spp. From the order of the Homoptera, for example, Myzus spp. and Psylla spp. From the order of the Lepidoptera, for example, *Ephestia kuehniella* and *Galleria mellonella*. From the order of the Coleoptera, for example, *Anobium punctatum, Rhizopertha dominica, Bruchidius obtectus, Acanthoscelides obtectus, Hylotrupes bajulus, Oryzaephilus surinamensis,* Sitophilus spp., Dermestes spp., Trogoderma spp., Anthrenus spp., Attagenus spp., Lyctus spp., Ptinus spp., *Niptus hololeucus, Gibbium psylloides,* Tribolium spp. and *Tenebrio molitor*. From the order of the Hymenoptera, for example, Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Gastrophilus spp., Hyppobosca spp., Stomoxys spp., Oestrus spp., Hypoderma spp. and Tabanus spp. From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro,* Argas spp., Ornithodoros spp., *Dermanyssus gallinae,* Boophilus spp., Rhipicephalus spp., Amblyomma spp., Hyalomma spp., Ixodes spp., Psoroptes spp., Chorioptes spp. and Sarcoptes spp.

The active compound combinations of the compounds of the formula (I) and the other active compounds can be converted to the customary formulations, such as solutions, emulsions, wettable powders, suspensions, powders, dusting agents, foams, pastes, soluble powders, aerosols, suspension-emulsion concentrates, natural and synthetic materials impregnated with active compound, very fine capsules in polymeric substances and formulations used with burning equipment, such as fumigating cartridges, fumigating cans, fumigating coils and the like, as well as ULV cold mist and warm mist formulations.

These formulations are produced in known manner, for example by mixing the active compound mixtures with extenders, that is, liquid solvents, liquefied gases under pressure, and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers: ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules: crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents: non-ionic and anionic emulsifiers, such as polyoxyethylene-fatty acid esters, polyoxyethylene-fatty alcohol ethers, for example alkylaryl polyglycol ethers and alkyl sulphonates; as dispersing agents: for example lignin- and sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium-oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general coptain between 0.1 and 95% by weight of active compound combination, preferably between 0.5 and 90%.

The active compound combinations according to the invention are used in the form of their commercially available formulations and/or in the use forms prepared from these formulations.

The total content of active compound (including synergist) of the use forms prepared from the commercially available formulations can vary within wide limits. The active compound concentration of the use forms can be from 0.001 to 95% by weight of active compound combination, preferably between 0.01 and 10% by weight.

The combinations are employed in a customary manner appropriate for the use forms.

When used against hygiene pests and pests of stored products, the active compound combinations are distinguished by an excellent residual action on wood and clay as well as a good stability to alkali on limed substrates.

knock-down effect is determined. If the $LT_{100}$ has not been reached after 6 hours, the percentage of knocked-down test insects is determined.

The active compounds, synergistic agents, concentrations of the active compounds, synergistic agents and mixtures and their actions can be seen from the following table.

TABLE 1

Examples of active compounds which can be used according to the invention

A. (Propoxur)

$$\text{structure with } O\text{-}C(=O)\text{-}NHCH_3 \text{ and } OC_3H_7i \text{ on benzene}$$

B. (Carbofuran)

benzofuran structure with $CH_3$, $CH_3$, and $O\text{-}CNHCH_3$ group

C. (Bendiocarb)

benzene with $O\text{-}C(=O)\text{-}NHCH_3$ and benzodioxole with two $CH_3$

D. (Decamethrin)

$Br_2C=CH\text{-}\overset{CH_3\ CH_3}{\underset{}{\triangle}}\text{-}C(=O)\text{-}CH(CN)\text{-}$ phenyl-O-phenyl E. (d-trans-Allethrin)

$\underset{CH_3}{\overset{CH_3}{>}}C=CH\text{-}\overset{CH_3\ CH_3}{\underset{}{\triangle}}\text{-}C(=O)\text{-}O\text{-}$cyclopentenone with $CH_3$ and $CH_2\text{-}CH=CH_2$ F. (Dichlorvos)

$CCl_2=CH\text{-}O\text{-}\overset{O}{\underset{\|}{P}}\text{-}(OCH_3)_2$

The activity of the compounds of the formula (I) which can be used according to the invention may be illustrated with the aid of the following biological examples:

TEST METHOD USED

$LT_{100}$ test

Test insects: Musca domestica ♀ ♀ Weymann's strain, (resistant)

Solvent: acetone

Solutions of the active compounds, synergistic agents and mixtures of active compounds and synergistic agents are prepared, and 2.5 ml thereof are pipetted onto filter paper discs 9.5 cm in diameter in Petri dishes. The filter paper absorbs the solutions. The Petri dishes remain uncovered until the solvent has evaporated completely. 25 test insects are then introduced into the Petri dishes and the dishes are covered with a glass lid.

The condition of the test insects is monitored continuously for up to 6 hours. The time required for a 100%

TABLE 2

Examples of synergistic agents which can be used according to the invention $$R^1\text{-}\underset{R^2}{\overset{R}{\underset{|}{C}}}\text{-}(CH_2)_m\text{-}NH\text{-}COOCH_2\text{-}C\equiv CH$$

| Synergistic Agent No. | R | $R^1$ | $R^2$ | n | Compound from Preparation Example No. |
|---|---|---|---|---|---|
| 1 | $CH_2F$ | $CH_2F$ | $CH_2F$ | 0 | 3 |
| 2 | $CH_2Cl$ | $CH_2Cl$ | $CH_2Cl$ | 0 | 4 |
| 3 | $CH_2F$ | $CH_2F$ | $CH_2F$ | 1 | 1 |
| 4 | $CH_2F$ | $CH_3$ | $CH_2F$ | 1 | 5 |
| 5 | $CH_2F$ | $CH_3$ | $CH_3$ | 1 | 6 |
| 6 | $CH_2Cl$ | $CH_3$ | $CH_2Cl$ | 0 | 7 |
| 7 | $CH_3$ | $CH_2Cl$ | $CH_3$ | 0 | 8 |
| 8 | $CH_2F$ | $CH_2F$ | $CH_3$ | 0 | 2 |
| 9 | $CH_2F$ | $CH_3$ | $CH_3$ | 0 | 9 |

TABLE 2-continued

Examples of synergistic agents which can be used according to the invention $$R^1-\underset{\underset{R^2}{|}}{\overset{\overset{R}{|}}{C}}-(CH_2)_m-NH-COOCH_2-C\equiv CH$$

| Synergistic Agent No. | R | $R^1$ | $R^2$ | n | Compound from Preparation Example No. |
|---|---|---|---|---|---|
| 10 | Piperonyl butoxide (prior art) | | | | |

TABLE 3

| Active compound | Synergistic agent | Test results Concentration in % Active compound | Synergistic agent | $LT_{100}$ in minutes or at 360' in % |
|---|---|---|---|---|
| A | — | 1.0 | — | 360' = 60% |
| B | — | 0.2 | — | 360' = 50% |
| C | — | 1.0 | — | 360' = 90% |
| D | — | 0.0016 | — | 150' |
| E | — | 0.04 | — | 120' |
| F | — | 0.008 | — | 105' |
| — | 1 | — | 0.2 | 360' = 90% |
| — | 2 | — | 1.0 | 360' = 40% |
| — | 3 | — | 1.0 | 360' = 35% |
| — | 4 | — | 0.2 | 360' = 90% |
| — | 5 | — | 0.2 | 360' |
| — | 6 | — | 0.2 | 180' |
| — | 7 | — | 0.2 | 210' |
| — | 8 | — | 0.2 | 360' = 20% |
| — | 9 | — | 0.2 | 360' = 20% |
| — | 10 | — | 1.0 | 360' = 0% |
| A + | 1 | 0.04 + | 0.04 | 90' |
| A + | 2 | 0.04 + | 0.04 | 105' |
| A + | 3 | 0.04 + | 0.04 | 90' |
| A + | 4 | 0.04 + | 0.04 | 90' |
| A + | 5 | 0.04 + | 0.04 | 75' |
| A + | 6 | 0.04 + | 0.04 | 75' |
| A + | 7 | 0.04 + | 0.04 | 90' |
| A + | 8 | 0.04 + | 0.04 | 90' |
| A + | 9 | 0.04 + | 0.04 | 75' |
| A + | 10 | 0.04 + | 0.04 | 360' = 80% |
| B + | 1 | 0.04 + | 0.04 | 90' |
| B + | 2 | 0.04 + | 0.04 | 90' |
| B + | 3 | 0.04 + | 0.04 | 90' |
| B + | 4 | 0.04 + | 0.04 | 75' |
| B + | 5 | 0.04 + | 0.04 | 90' |
| B + | 6 | 0.04 + | 0.04 | 75' |
| B + | 7 | 0.04 + | 0.04 | 75' |
| B + | 8 | 0.04 + | 0.04 | 90' |
| B + | 9 | 0.04 + | 0.04 | 90' |
| B + | 10 | 0.04 + | 0.04 | 360' = 45% |
| C + | 1 | 0.04 + | 0.04 | 120' |
| C + | 2 | 0.04 + | 0.04 | 150' |
| C + | 3 | 0.04 + | 0.04 | 150' |
| C + | 4 | 0.04 + | 0.04 | 120' |
| C + | 5 | 0.04 + | 0.04 | 90' |
| C + | 6 | 0.04 + | 0.04 | 90' |
| C + | 7 | 0.04 + | 0.04 | 120' |
| C + | 8 | 0.04 + | 0.04 | 120' |
| C + | 9 | 0.04 + | 0.04 | 120' |
| C + | 10 | 0.04 + | 0.2 | 360' = 90% |
| D + | 2 | 0.0016 + | 0.0016 | 105' |
| D + | 4 | 0.0016 + | 0.0016 | 90' |
| D + | 5 | 0.0016 + | 0.0016 | 105' |
| D + | 6 | 0.0016 + | 0.0016 | 120' |
| D + | 7 | 0.0016 + | 0.0016 | 105' |
| D + | 8 | 0.0016 + | 0.0016 | 105' |
| D + | 9 | 0.0016 + | 0.0016 | 105' |
| D + | 10 | 0.0016 + | 0.0016 | 150' |
| E + | 2 | 0.04 + | 0.04 | 45' |
| E + | 4 | 0.04 + | 0.04 | 45' |
| E + | 5 | 0.04 + | 0.04 | 30' |
| E + | 6 | 0.04 + | 0.04 | 45' |
| E + | 7 | 0.04 + | 0.04 | 45' |
| E + | 8 | 0.04 + | 0.04 | 45' |

TABLE 3-continued

| Active compound | Synergistic agent | Test results Concentration in % Active compound | Synergistic agent | $LT_{100}$ in minutes or at 360' in % |
|---|---|---|---|---|
| E + | 10 | 0.04 + | 0.04 | 60' |
| F + | 3 | 0.008 + | 0.008 | 75' |
| F + | 4 | 0.008 + | 0.008 | 75' |
| F + | 6 | 0.008 + | 0.008 | 75' |
| F + | 8 | 0.008 + | 0.008 | 75' |
| F + | 9 | 0.008 + | 0.008 | 75' |
| F + | 10 | 0.008 + | 0.008 | 90' |

The preparation of the compounds according to the invention may be illustrated with the aid of the following preparation examples:

EXAMPLE 1

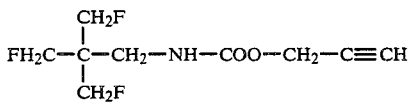

O-2-Propinyl N-(2,2-bisfluoromethyl-3-fluoropropyl)carbamate 16.7 g of 2,2-bisfluoromethyl-3-fluoropropyl isocyanate (29% strength solution in toluene) are dissolved in 100 ml of toluene, and 10 mg of diazabicyclooctane (dabco) are added. 5.6 g of 2-propinyl alcohol are added dropwise to this reaction mixture at room temperature (about 20° C.). After the reaction mixture has been heated at the boiling point for four hours, it is cooled and washed with water. After drying over sodium sulphate, the solvent is distilled off and the oil which remains is freed from residual solvent under a high vacuum. 22 g of O-2-propinyl N-(2,2-bisfluoromethyl-3-fluoropropyl)-carbamate are obtained in the form of a colorless oil (80% of theory yield), $n_D^{20}$: 1.4505

EXAMPLE 2

O-2-Propinyl N-(1,1-bisfluoromethyl-ethyl)-carbamate

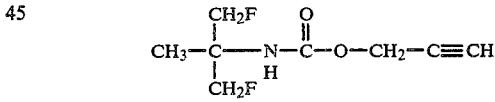

14 g (0.1 mol) of 2,2-bisfluoromethylpropionyl fluoride are dissolved in 200 ml of acetone. A solution of 6.5 g (0.1 mol) of sodium azide in 20 ml of water is added dropwise at 0° C., the mixture is stirred at room temperature for one hour and 200 ml of water are added. The aqueous phase is extracted twice with 200 ml of toluene each time and the resulting combined toluene phase is washed twice with 200 ml of water each time. After drying over sodium sulphate, the toluene phase is slowly heated to 70°-80° C., until the evolution of gas which starts ends. The mixture is then boiled under reflux for one hour. Completion of the formation of 1,1-bisfluoromethyl-ethyl isocyanate is monitored by IR spectroscopy (decrease$\approx CON_3$=2120 cm$^{-1}$, increase$\approx$N=C=O=2250 cm$^{-1}$). 11.2 g of 2-propinyl alcohol are added dropwise to the 1,1-bisfluoromethyl-ethyl isocyanate solution obtained in this manner, 10 mg of diazabicyclooctane (dabco) are added and the subsequent procedure is as under Preparation Example 1.

13 g of O-2-propinyl N-(1,1-bisfluoromethylethyl)-carbamate are obtained in the form of a colorless oil (68% of the theory yield), $n_D^{20}$: 1.4430

The compounds of the following examples are obtained analogously to Examples 1 and 2:

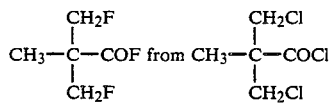

| Example No. | R | $R^1$ | $R^2$ | n | Refractive index $n_D^{20}$ or melting point °C. |
|---|---|---|---|---|---|
| 3 | $CH_2F$ | $CH_2F$ | $CH_2F$ | 0 | 1.4371 |
| 4 | $CH_2Cl$ | $CH_2Cl$ | $CH_2Cl$ | 0 | 55 |
| 5 | $CH_2F$ | $CH_3$ | $CH_2F$ | 1 | 1.4505 |
| 6 | $CH_3$ | $CH_2F$ | $CH_3$ | 1 | 1.4580 |
| 7 | $CH_2Cl$ | $CH_3$ | $CH_2Cl$ | 0 | 1.4952 |
| 8 | $CH_3$ | $CH_2Cl$ | $CH_3$ | 0 | 1.4757 |
| 9 | $CH_2F$ | $CH_3$ | $CH_3$ | 0 | 1.4470 |

The intermediates (or their precursors) which can be used according to the invention can be prepared according to the following examples:

EXAMPLE 1A

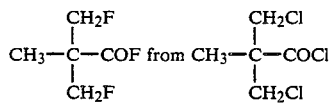

947.5 g (5 mols) of dichloropivaloyl chloride, 2 kg of tetramethylene sulphone and 1.16 kg (20 mols) of potassium fluoride are heated at 230° C. in a VA stirred autoclave at an initial pressure of 2 bar of $N_2$ for 5 hours and the mixture is cooled, let down and distilled under slightly reduced pressure. 576 g (79.2% of theory) of difluoropivaloyl fluoride (boiling point 110–120 mbar 52°–56° C.) are obtained. In the 3 kg scale in a paddle reactor, yields of between 85 and 90% of theory are obtained.

EXAMPLE 2A

900 g (4 mols) of trischloromethylacetyl chloride (trichloropivaloyl chloride), 1.16 kg (20 mols) of potassium fluoride and 2,250 ml of tetramethylene sulphone are stirred at 200° C. under normal pressure for 5 hours, the mixture is cooled, 1 liter of xylene is added and the mixture is distilled up to the boiling point of the tetramethylene sulphone. The xylene solution contains the entire trisfluoromethylacetyl fluoride (80% of theory), which, because of its melting point of 50°–52° C. and the boiling point of 48° C./22 mbar and the high reactivity of the acid fluoride, is in general further reacted directly in the solution.

EXAMPLE 3A

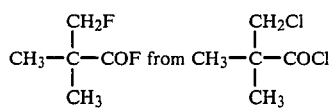

5.8 kg (100 mols) of potassium fluoride and 7.7 kg of tetramethylene sulphone are initially introduced into a 20 liter paddle reactor with a distillation attachment and are subjected to incipient distillation under about 20 mbar, 10% of the solvent used being removed. The reactor is gassed with $N_2$, the internal temperature is allowed to fall from 150° to 125°–130° C., 6.2 kg (40 mols) of chloropivaloyl chloride are sucked in and the apparatus is flushed with $N_2$ and closed pressure-tight. After 3 bar of $N_2$ has been forced in, the mixture is warmed at 150° C. for 1 hour and at 230° C. for 12 hours, cooled to 80° C. and distilled under 100 mbar. 3.256 kg (68% of theory) of fluoropivaloyl fluoride (boiling point 40°–41° C./100 mbar) and 1.4 kg (26%) of chloropivaloyl fluoride (boiling point 65° C./100 mbar), as a by-product, are obtained. The result corresponds to a selectivity of 92% for 74% conversion.

EXAMPLE 1B

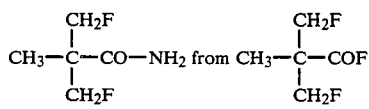

700 g of 25% strength (% by weight) aqueous ammonia solution and 500 g of ice are taken and 515 g (3.7 mols) of difluoropivaloyl fluoride (bisfluoromethylpropionyl fluoride)), dissolved in 250 ml of $CH_2Cl_2$, are added dropwise. The mixture is allowed to after-react at about 10° C. for 15 minutes and the precipitate is filtered off with suction, washed with a little cold water and dried at 70° C. under reduced pressure. Yield: 451 g (89% of theory) of bisfluoromethylpropionic acid amide; melting point: 100°–101° C.

EXAMPLE 2B

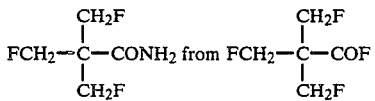

Trifluoromethylacetamide is obtained in a yield of >95% of theory from trifluoromethylacetyl fluoride (trifluoropivaloyl fluoride) at a reaction temperature of 40°–50° C. in a manner analogous to that described in Example 1, but with xylene as the solvent. Melting point: 114°–115° C.

EXAMPLE 3B

250 g (1.6 mols) of trifluoromethylacetamide and 284 g (2 mols) of $P_2O_5$ are mixed thoroughly and the mixture is heated under about 70 mbar at an external temperature of 160°-200° C., whereupon the nitrile distils off. The experiment is repeated in the same reaction vessel using the residue, and a total of 434 g (98% of theory) of trisfluoromethylacetonitrile are obtained; boiling point: 90° C./58 mbar; melting point: 70°-75° C.

EXAMPLE 4B

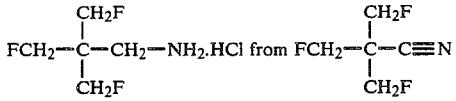

30 g (0.218 mol) of trisfluoromethylacetonitrile are dissolved in 180 ml of methanol and hydrogenated in the presence of 10 g of Raney nickel (Ni/Fe 85:15) under 80-90 bar of H₂ at a temperature of 38°-40° C. The mixture is filtered and the filtrate is freed from methanol, to dryness, under a waterpump vacuum. 36 g (93% of theory) of trifluoroneopentylamine hydrochloride are obtained.

EXAMPLE 5B

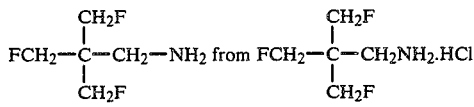

106.5 g (0.6 mol) of trifluoroneopentylamine hydrochloride are introduced into a solution of 200 g of 50% strength KOH in 40 ml of H₂O, while cooling with ice, and the free amine is extracted by shaking with 250 ml of ether, the extract is dried with MgSO₄ and concentrated and the solid residue is dried under reduced pressure at 20° C. for 1 hour. Yield of free amine: 66 g (78% of theory); melting point: 66°-67° C.; boiling point: 74° C./52 mbar.

EXAMPLE 6B

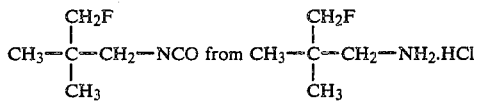

300 ml of chlorobenzene are saturated with phosgene (COCl₂) at 20° C., 110.6 g (0.7 mol) of 3-fluoro-2,2-dimethylpropylamine hydrochloride (monofluoroneopentylamine hydrochloride) are added and the mixture is slowly heated up to the reflux temperature, while continuously adding phosgene. When the splitting off of HCl has ended, N₂ is passed through for about a further 2 hours and the mixture is then distilled. Yield of monofluoroneopentyl isocyanate: 95 g (92% of theory); boiling point: 52° C./20 mbar.

The other intermediates (or their precursors) which can be used according to the invention can be obtained analogously.

It will be understood that the specification and examples are illustrative but not limitative of the present invention and that other embodiments within the spirit and scope of the invention will suggest themselves to those skilled in the art.

We claim:

1. A halogenoalkylcarbamic acid ester of the formula

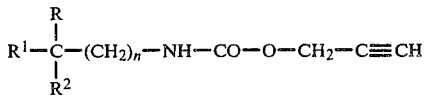

in which R, $R^1$ and $R^2$ independently of one another represent methyl which is optionally substituted by fluorine or chlorine, at least one of the methyl groups R, $R^1$ and $R^2$ being substituted by at least one fluorine or chlorine atom, and n represents 0 or 1.

2. A compound according to claim 1, in which
R, $R^1$ and $R^2$ independently of one another represent CH₃, CH₂Cl and/or CH₂F, at least one of the radicals R, $R^1$ and $R^2$ representing CH₂Cl or CH₂F.

3. A compound according to claim 1, in which
R, $R^1$ and $R^2$ independently of one another represent CH₃ or CH₂F, at least one of the radicals R, $R^1$ and $R^2$ representing CH₂F.

4. A compound according to claim 1 wherein such compound is O-2-propinyl N-(2,2-bisfluoromethyl-3-fluoropropyl)-carbamate of the formula

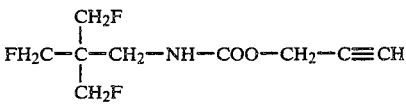

5. A compound according to claim 1 wherein such compound is O-2-propinyl N-(1,1-bisfluoromethyl-ethyl)-carbamate of the formula

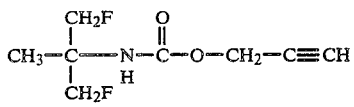

6. A compound according to claim 1 wherein such compound is O-2-propinyl N-(1,1-bisfluoromethyl-2-fluoroethyl)-carbamate of the formula

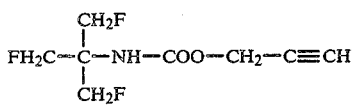

7. A compound according to claim 1 wherein such compound is O-2-propinyl N-(1,1-bischloromethyl-2-chloroethyl-carbamate of the formula

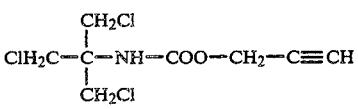

8. A compound according to claim 1 wherein such compound is O-2-propinyl N-(2,2-bisfluoromethyl-propyl)-carbamate of the formula

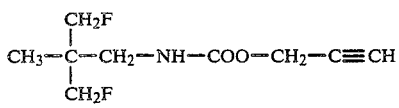

9. An arthropodicidal composition comprising an arthropodicidally effective amount of a known arthropodicide plus a synergistically effective amount of a compound according to claim 1.

10. A composition according to claim 9, wherein the synergist is

O-2-propinyl N-(2,2-bisfluoromethyl-3-fluoropropyl)-carbamate,

O-2-propinyl N-(1,1-bisfluoromethyl-ethyl)-carbamate,

O-2-propinyl N-(1,1-bisfluoromethyl-2-fluoroethyl)-carbamate,

O-2-propinyl N-(1,1-bischloromethyl-2-chloroethyl)-carbamate or

O-2-propinyl N-(2,2-bisfluoromethyl-propyl)-carbamate.

11. A method of combating arthropods which comprises administering to such arthropods or to an arthropod habitat an arthropodically effective amount of a composition comprising an arthropodically effective amount of a known arthropodicide plus a synergistically effective amount of a halogenoalkylcarbamic acid ester of the formula

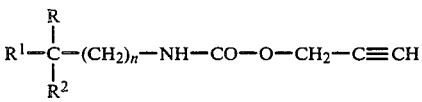

in which R, $R^1$ and $R^2$ independently of one another represent methyl which is optionally substituted by fluorine or chlorine, at least one of the methyl groups R, $R^1$ and $R^2$ being substituted by at least one fluorine or chlorine atom, and n represents 0 or 1.

12. A method of combating arthropods which comprises administering to such arthropods or to an arthropod habitat an arthropodically effective amount of a known arthropodicide plus a synergistically effective amount of a compound selected from the group consisting of O-2-propinyl N-(2,2-bisfluoromethyl-3-fluoropropyl)-carbamate, O-2-propinyl N-(1,1-bisfluoromethyl-ethyl)-carbamate, O-2-propinyl N-(1,1-bisfluoromethyl-2-fluoroethyl)-carbamate, O-2-propinyl N-(1,1-bischloromethyl-2-chloroethyl)-carbamate and O-2-propinyl N-(2,2-bisfluoromethyl-propyl)-carbamate.

* * * * *